(12) United States Patent
Hood et al.

(10) Patent No.: US 8,583,247 B1
(45) Date of Patent: Nov. 12, 2013

(54) METHODS AND SYSTEMS FOR PROVIDING VISUAL CUES TO ASSIST IN FITTING A COCHLEAR IMPLANT PATIENT

(75) Inventors: Kevin Hood, Coquitlam (CA);
Fernando Chapa, Harold, CA (US);
Guillermo A. Calle, Moorpark, CA (US); Jacob Johnston, Winnetka, CA (US)

(73) Assignee: Advanced Bionics AG, Zug (CH)

( * ) Notice: Subject to any disclaimer, the term of this patent is extended or adjusted under 35 U.S.C. 154(b) by 670 days.

(21) Appl. No.: 12/847,151

(22) Filed: Jul. 30, 2010

(51) Int. Cl.
*A61N 1/36* (2006.01)

(52) U.S. Cl.
USPC ............................................ 607/57; 607/137

(58) Field of Classification Search
None
See application file for complete search history.

(56) References Cited

U.S. PATENT DOCUMENTS

| | | | |
|---|---|---|---|
| 5,544,150 A * | 8/1996 | Fujimoto et al. | 370/248 |
| 2007/0172047 A1 * | 7/2007 | Coughlan et al. | 379/202.01 |
| 2008/0228243 A1 * | 9/2008 | Maltan et al. | 607/57 |
| 2009/0018616 A1 * | 1/2009 | Quick et al. | 607/57 |

* cited by examiner

*Primary Examiner* — Brian T Gedeon
*Assistant Examiner* — Ankit Tejani
(74) *Attorney, Agent, or Firm* — ALG Intellectual Property, LLC

(57) ABSTRACT

An exemplary method of fitting a cochlear implant patient includes a fitting station detecting a user input associated with a sound processor of a cochlear implant system, wherein the sound processor is communicatively coupled to the cochlear implant fitting station by way of a communication path, and transmitting a signal to the sound processor by way of the communication path in response to the detecting of the user input, the signal configured to direct the sound processor to display a visual cue. Corresponding methods and systems are also described.

18 Claims, 12 Drawing Sheets

METHODS AND SYSTEMS FOR PROVIDING VISUAL CUES TO ASSIST IN FITTING A COCHLEAR IMPLANT PATIENT

BACKGROUND INFORMATION

The natural sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea, which are needed to transduce acoustic signals into auditory nerve impulses. People who suffer from sensorineural hearing loss may be unable to derive significant benefit from conventional hearing aid systems, no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers by way of one or more channels formed by an array of electrodes implanted in the cochlea. Direct stimulation of the auditory nerve fibers leads to the perception of sound in the brain and at least partial restoration of hearing function.

When a cochlear implant system is initially implanted in a patient, and during follow-up tests and checkups thereafter, it is usually necessary to "fit" the cochlear implant system to the patient. Fitting of a cochlear implant system to a patient is typically performed by an audiologist or the like who presents various stimuli to the patient and relies on subjective feedback from the patient as to how such stimuli are perceived. Adjustments may be made to specifically tailor the parameters of the cochlear implant system to the patient being fitted.

Fitting a cochlear implant system to a patient typically requires multiple pieces of fitting hardware. For example, a clinician's programming interface ("CPI"), its power supply, and various cables are typically required to communicatively couple a fitting station to a sound processor of a cochlear implant system in order to fit the cochlear implant system to a patient. If the patient is a bilateral cochlear implant patient (i.e., has a separate cochlear implant system for each ear), the number of fitting hardware components is more or less doubled. The combination of sound processors, connection cables, and other pieces of hardware can create confusion for an audiologist during the fitting process. For example, it may be difficult for an audiologist to organize the multiple hardware components to ensure the different pieces of hardware are properly connected.

Even if the hardware components are well organized, it may be difficult for an audiologist to ascertain which serial port or USB adapter of a fitting station is responsible for transmitting data to a specific cochlear implant or sound processor at a given moment in time. To further exacerbate the problem, the serial port may be associated with a serial port number that may be dynamically and transparently assigned by the operating system of the fitting station. As a result, it can be difficult for an audiologist to accurately map between hardware components and corresponding software operations performed by a fitting station.

These problems might lead the audiologist to make mistakes when trying to coordinate activities between a fitting station and connected hardware components. For example, an audiologist might accidentally reformat the wrong sound processor or inadvertently overstimulate a cochlear implant based on data from another cochlear implant.

SUMMARY

An exemplary method of fitting a cochlear implant patient includes a cochlear implant fitting station 1) detecting a user input associated with a sound processor of a cochlear implant system, wherein the sound processor is communicatively coupled to the cochlear implant fitting station by way of a communication path, and 2) transmitting a signal to the sound processor by way of the communication path, the signal configured to direct the sound processor to display a visual cue in response to the detecting.

Another exemplary method of fitting a cochlear implant patient includes a cochlear implant fitting station communicatively coupled to a first clinician's programming interface ("CPI") device and a first sound processor by way of a first communication path and communicatively coupled to a second CPI device and a second sound processor by way of a second communication path 1) detecting a first user input associated with the first sound processor and 2) transmitting, in response to the detecting of the first user input, a first signal to the first CPI device and to the first sound processor by way of the first communication path, the first signal configured to direct the first sound processor and the first CPI device to display at least one visual cue.

An exemplary system for fitting a bilateral cochlear implant patient includes 1) a cochlear implant fitting station, 2) a first sound processor communicatively coupled to the cochlear implant fitting station by way of a first communication path, and 3) a second sound processor communicatively coupled to the cochlear implant fitting station by way of a second communication path, wherein the cochlear implant fitting station is configured to detect a first user input associated with the first sound processor and transmit a first signal to the first sound processor by way of the first communication path, the first signal configured to direct the first sound processor to display a first visual cue.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers may designate identical or similar elements.

DETAILED DESCRIPTION

Methods and systems for presenting visual cues to assist in fitting a cochlear implant patient are described herein. As described in more detail below, a fitting station may be configured to detect a user input associated with a sound processor communicatively coupled to the fitting station by way of a communication path. The fitting station may be further configured to transmit, by way of the communication path, a signal to the sound processor. The signal may be configured to direct the sound processor to display a visual cue.

As used herein, a "visual cue" refers to any visual indication that may be seen by a user of a fitting station used to fit a cochlear implant patient. A visual cue may include an illumination of a light emitting device (e.g., a light bulb, a light emitting diode ("LED"), a display screen, etc). In some examples, a visual cue may blink intermittently at a rate that is the same or different than another visual cue. In addition, visual cues may include any one or combination of different colors (e.g., by way of one or more multi-color LEDs).

Numerous advantages may be associated with the methods and systems described herein. An audiologist may utilize one or more visual cues to accurately map between one or more operations of a fitting subsystem and one or more operations of corresponding hardware components connected to the fitting subsystem. For example, the audiologist may utilize one or more visual cues to visually verify which hardware components are performing or going to perform a requested fitting operation. As a result, the audiologist may visually confirm the cochlear implant being affected by each fitting operation (e.g., whether the fitting operation is being performed on or by a first or second cochlear implant).

Figure 1:
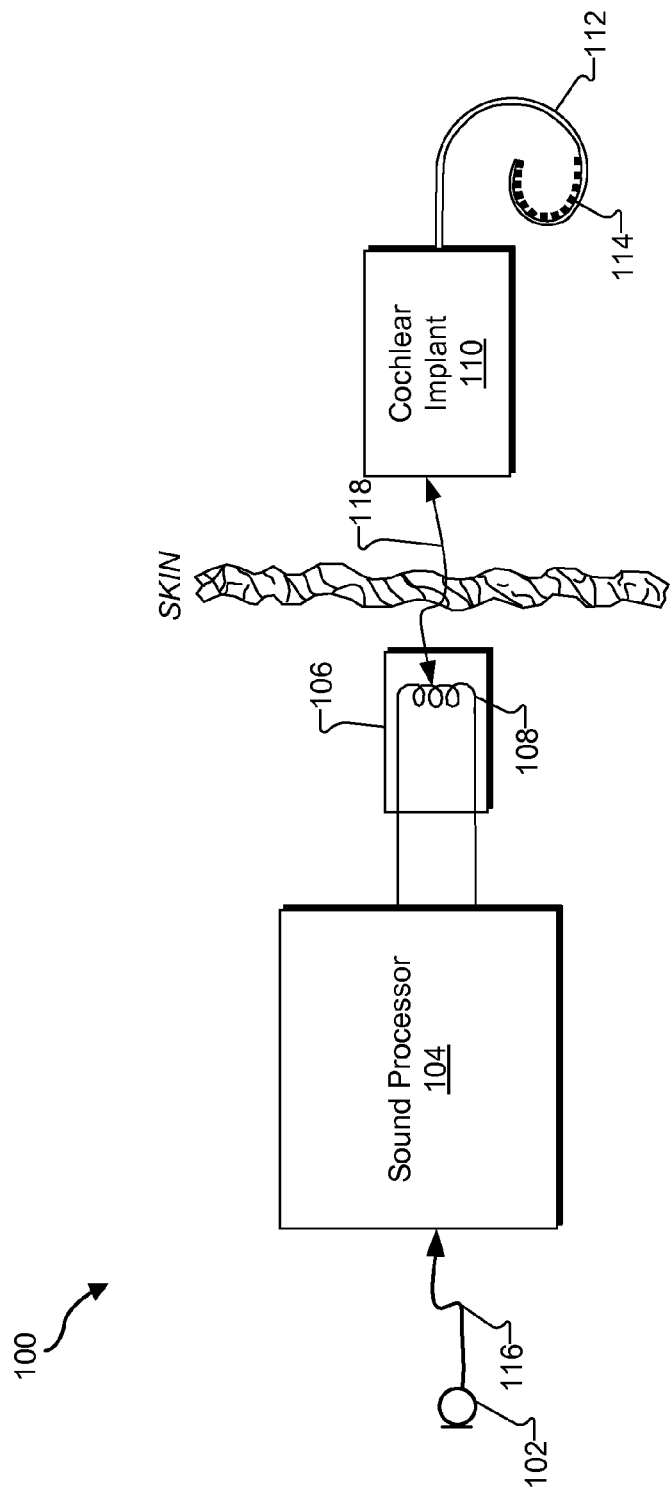
FIG. 1 illustrates an exemplary cochlear implant system according to principles described herein.

To facilitate an understanding of the methods and systems described herein, an exemplary cochlear implant system 100 will be described in connection with FIG. 1. As shown in FIG. 1, cochlear implant system 100 may include a microphone 102, a sound processor 104, a headpiece 106 having a coil 108 disposed therein, a cochlear implant 110 (also referred to as an "implantable cochlear stimulator"), and a lead 112 with a plurality of electrodes 114 disposed thereon. Additional or alternative components may be included within cochlear implant system 100 as may serve a particular implementation.

As shown in FIG. 1, microphone 102, sound processor 104, and headpiece 106 may be located external to a cochlear implant patient. In some alternative examples, microphone 102 and/or sound processor 104 may be implanted within the patient. In such configurations, the need for headpiece 106 may be obviated.

Microphone 102 may detect an audio signal and convert the detected signal to a corresponding electrical signal. The electrical signal may be sent from microphone 102 to sound processor 104 via a communication link 116, which may include a telemetry link, a wire, and/or any other suitable communication link.

Sound processor 104 is configured to direct cochlear implant 110 to generate and apply electrical stimulation (also referred to herein as "stimulation current") to one or more stimulation sites within a cochlea of the patient. To this end, sound processor 104 may process the audio signal detected by microphone 102 in accordance with a selected sound processing strategy to generate appropriate stimulation parameters for controlling cochlear implant 110. Sound processor 104 may include or be implemented by a behind-the-ear ("BTE") unit, a portable speech processor ("PSP"), and/or any other sound-processing unit as may serve a particular implementation. Exemplary components of sound processor 104 will be described in more detail below.

Sound processor 104 may be configured to transcutaneously transmit, in accordance with a sound processing program associated with cochlear implant 110, one or more control parameters and/or one or more power signals to cochlear implant 110 with coil 108 by way of a communication link 118. These control parameters may be configured to specify one or more stimulation parameters, operating parameters, and/or any other parameter by which cochlear implant 110 is to operate as may serve a particular implementation. Exemplary control parameters include, but are not limited to, stimulation current levels, volume control parameters, program selection parameters, operational state parameters (e.g., parameters that turn a sound processor and/or a cochlear implant on or off), audio input source selection parameters, fitting parameters, noise reduction parameters, microphone sensitivity parameters, microphone direction parameters, pitch parameters, timbre parameters, sound quality parameters, most comfortable current levels ("M levels"), threshold current levels ("T levels"), channel acoustic gain parameters, front and backend dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Sound processor 104 may also be configured to operate in accordance with one or more of the control parameters.

As shown in FIG. 1, coil 108 may be housed within headpiece 106, which may be affixed to a patient's head and positioned such that coil 108 is communicatively coupled to a corresponding coil included within cochlear implant 110. In this manner, control parameters and power signals may be wirelessly transmitted between sound processor 104 and cochlear implant 110 via communication link 118. It will be understood that data communication link 118 may include a bi-directional communication link and/or one or more dedicated uni-directional communication links. In some alternative embodiments, sound processor 104 and cochlear implant 110 may be directly connected with one or more wires or the like.

Cochlear implant 110 may be configured to generate electrical stimulation representative of an audio signal detected by microphone 102 in accordance with one or more stimulation parameters transmitted thereto by sound processor 104. Cochlear implant 110 may be further configured to apply the electrical stimulation to one or more stimulation sites within the cochlea via one or more electrodes 114 disposed along lead 112. In some examples, cochlear implant 110 may include a plurality of independent current sources each associated with a channel defined by one or more of electrodes 114. In this manner, different stimulation current levels may be applied to multiple stimulation sites simultaneously by way of multiple electrodes 114. In such examples, cochlear implant system 100 may be referred to as a "multi-channel cochlear implant system."

To facilitate application of the electrical stimulation generated by cochlear implant 110, lead 112 may be inserted within a duct of the cochlea such that electrodes 114 are in communication with one or more stimulation sites within the cochlea. As used herein, the term "in communication with" refers to electrodes 114 being adjacent to, in the general vicinity of, in close proximity to, directly next to, or directly on the stimulation site. Any number of electrodes 114 (e.g., sixteen) may be disposed on lead 112 as may serve a particular implementation.

Figure 2:
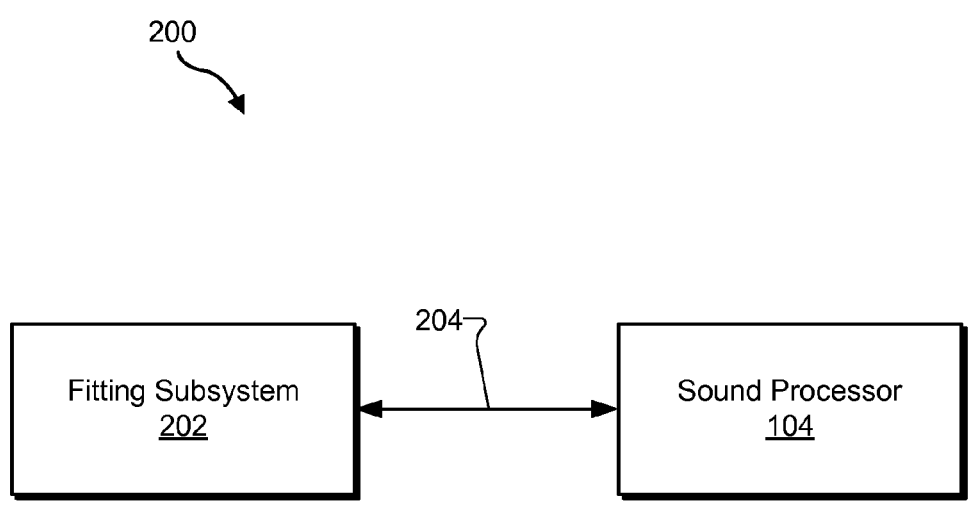
FIG. 2 illustrates an exemplary cochlear implant fitting system according to principles described herein.

FIG. 2 illustrates an exemplary cochlear implant fitting system 200 (or simply "fitting system 200") that may be used to fit a cochlear implant patient. As used herein, the terms "fitting a cochlear implant patient" and "fitting a cochlear implant to a patient" will be used interchangeably to refer to performing one or more fitting operations associated with sound processor 104, cochlear implant 110, and/or any other component of cochlear implant system 100 in order to optimize performance of cochlear implant system 100 for the patient. Such fitting operations may include, but are not limited to, adjusting one or more control parameters by which sound processor 104 and/or cochlear implant 110 operate, measuring one or more electrode impedances, performing one or more neural response detection operations, and/or performing one or more diagnostics procedures associated with the cochlear implant system.

As shown in FIG. 2, fitting system 200 may include a fitting subsystem 202 configured to be selectively and communicatively coupled to sound processor 104 of cochlear implant system 100 by way of a communication link 204. Fitting subsystem 202 and sound processor 104 may communicate using any suitable communication technologies, devices, networks, media, and protocols supportive of data communications.

Fitting subsystem 202 may be configured to perform one or more of the fitting operations described herein. To this end, fitting subsystem 202 may be implemented by any suitable combination of computing and communication devices including, but not limited to, a fitting station, a personal computer, a laptop computer, a handheld device, a mobile device (e.g., a mobile phone), a clinician's programming interface ("CPI") device, and/or any other suitable component as may serve a particular implementation.

Figure 3:
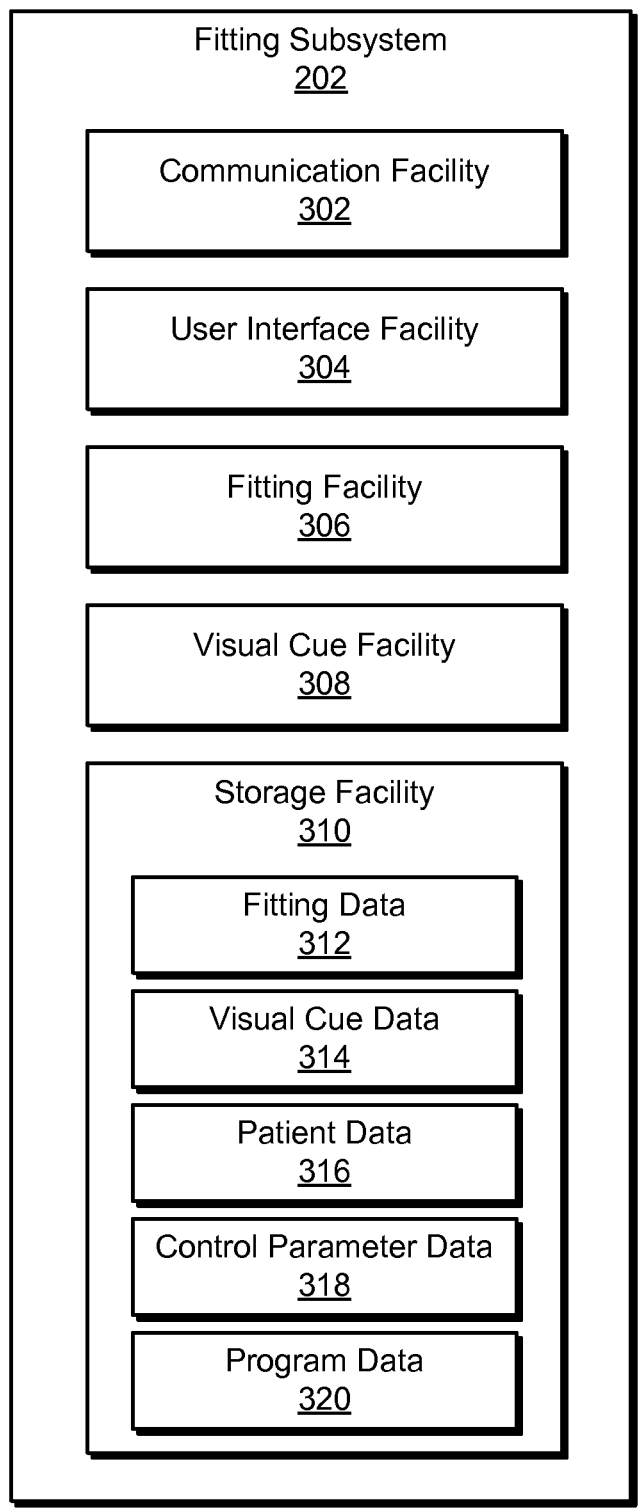
FIG. 3 illustrates exemplary components of an exemplary fitting subsystem according to principles described herein.

FIG. 3 illustrates exemplary components of fitting subsystem 202. As shown in FIG. 3, fitting subsystem 202 may include a communication facility 302, a user interface facility 304, a fitting facility 306, a visual cue facility 308, and a storage facility 310, which may be communicatively coupled to one another using any suitable communication technologies. Each of these facilities will now be described in more detail.

Communication facility 302 may be configured to facilitate communication between fitting subsystem 202 and cochlear implant system 100 (e.g., sound processor 104 and/or cochlear implant 110) by way of a communication path. The communication path may include any suitable combination of components configured to allow fitting subsystem 202 to interface and communicate with sound processor 104. For example, the communication path may include one or more cables and/or intermediary hardware devices (e.g., a CPI device) configured to allow fitting subsystem 202 to interface and communicate with sound processor 104. Communication facility 302 and/or the communication path may additionally or alternatively include one or more transceiver components configured to wirelessly transmit data (e.g., program data and/or control parameter data) to sound processor 104 and/or wirelessly receive data (e.g., feedback data, impedance measurement data, neural response data, etc.) from sound processor 104. The wireless communication between communication facility 302 and sound processor 104 may be achieved using any suitable communication technologies (e.g., Bluetooth).

In some examples (e.g., during a fitting of a bilateral cochlear implant patient), communication facility 302 may facilitate selective and/or concurrent communication between multiple sound processors (e.g., right and left sound processors). In this manner, communication facility 302 may be configured to communicate with a first cochlear implant associated with a first ear (e.g., the right ear) of the patient by way of a first sound processor and a second cochlear implant associated with a second ear (e.g., the left ear) of the patient by way of a second sound processor. Communication facility 302 may also be configured to communicate with any intermediary hardware devices disposed along one or more communication paths coupling one or more sound processors to fitting subsystem 202.

Communication facility 302 may additionally or alternatively be configured to facilitate communication between fitting subsystem 202 and one or more other devices. For example, communication facility 302 may be configured to facilitate communication between fitting subsystem 202 and one or more computing devices (e.g., by way of the Internet and/or one or more other types of networks), reference implants, and/or any other computing device as may serve a particular implementation.

User interface facility 304 may be configured to provide one or more user interfaces configured to facilitate user interaction with fitting subsystem 202. For example, user interface facility 304 may provide a graphical user interface ("GUI") through which one or more functions, options, features, and/or tools associated with one or more fitting operations described herein may be provided to a user and through which user input may be received. In certain embodiments, user interface facility 304 may be configured to provide the GUI to a display device (e.g., a computer monitor) for display. In some examples, user interface facility 304 may be configured to provide a graphical user interface configured to graphically indicate one or more fitting operations and/or one or more visual cues associated with the fitting operation(s), as will be described in more detail below.

In some examples, user interface facility 304 may be configured to detect a user input associated with a sound processor or cochlear implant communicatively coupled to fitting subsystem 202 by way of a communication path. For example, user interface facility 304 may be configured to detect that fitting subsystem 202 has received a user input command (e.g., provided by a user of fitting subsystem 202) to perform one or more fitting operations by way of the sound processor. Additionally or alternatively, user interface facility 304 may be configured to detect a user input command requesting a visual cue be displayed by the sound processor. In response to a detected user input, fitting subsystem 202 may be configured to facilitate display of one or more visual cues (e.g., by directing the sound processor to display a visual cue), as will be described in more detail below.

Fitting facility 306 may be configured to perform one or more fitting operations. For example, fitting facility 306 may be configured to adjust one or more control parameters by which sound processor 104 and/or cochlear implant 110 operate, direct sound processor 104 to measure one or more electrode impedances, perform one or more neural response detection operations, and/or perform one or more diagnostics procedures associated with cochlear implant system 100.

Fitting facility 306 may additionally or alternatively be configured to use a sound processor (e.g., sound processor 104) to selectively fit a cochlear implant (e.g., cochlear implant 110) to a cochlear implant patient. For example, fitting facility 306 may be configured to use sound processor 104 to perform one or more fitting operations associated with cochlear implant 110 or a corresponding cochlear implant patient.

Visual cue facility 308 may be configured to facilitate the display of one or more visual cues configured to assist a user (e.g., an audiologist) of fitting subsystem 202. For example, visual cue facility 308 may be configured to direct one or more hardware components (e.g., a fitting station, a sound processor, a CPI device, etc.) to display one or more visual cues configured to indicate any suitable information to the user. In some examples, the visual cues may be configured to identify a communicative coupling of one hardware component (e.g., a fitting station) to another hardware component (e.g., a sound processor). Additionally or alternatively, the visual cues may be configured to identify an association between an operation of one hardware component (e.g., a software operation performed by a fitting station) and a corresponding operation of another hardware component (e.g., a fitting operation performed by a sound processor in response to the software operation of the fitting station). Using the visual cues, a user of fitting subsystem 202 may visually verify that the hardware components are properly connected and that the intended hardware components are performing the intended operations, as will be explained in more detail below.

To facilitate display of one or more visual cues, visual cue facility 308 may be configured to transmit (e.g., by way of communication facility 302) a signal configured to direct a sound processor and/or other hardware components to display one or more visual cues. For example, visual cue facility 308 may be configured to transmit a signal configured to override a normal operation of a sound processor's LED to selectively illuminate the LED to display a visual cue. To illustrate, the sound processor may include an LED that operates in accordance with one or more normal operations. For example, the LED may be configured to selectively illuminate to indicate a battery level of the sound processor, to indicate that the sound processor is communicatively coupled (or "locked") to a cochlear implant, and/or to indicate that the sound processor is powered on. A normal operation of the LED may additionally and/or alternatively include any other operation as may serve a particular implementation. The signal transmitted by visual cue facility 308 may be configured to override the normal operation of the LED to selectively illuminate the LED to provide the visual cue.

In some examples, visual cue facility 308 may be configured to control one or more visual attributes of the visual cue. For example, the signal transmitted by visual cue facility 308 may control a timing of the visual cue (e.g., the signal may ensure that the LED illuminates at the same time as or just prior to a corresponding fitting operation), a blinking of the visual cue (e.g., the signal may control a rate at which the LED blinks), and/or a color of the visual cue (e.g., if the LED is a multi-color LED, the signal may control the color in which the LED illuminates).

Additionally or alternatively, visual cue facility 308 may be configured direct a CPI device (e.g., a CPI device within a communication path between fitting subsystem 202 and the sound processor) to display an additional visual cue. For example, the signal transmitted by visual cue facility 308 may be configured to override a normal operation of an LED of the CPI device to display the additional visual cue. In some examples, the additional visual cue displayed by the CPI device may correspond to the visual cue displayed by the sound processor (e.g., the two visual cues may be given at the same time, may blink at the same rate, and/or may have the same color).

In configurations in which fitting subsystem 202 is used to fit a bilateral cochlear implant patient, visual cue facility 308 may be configured to facilitate the display of visual cues by two sound processors and/or corresponding fitting hardware components being used to fit two cochlear implants to the patient. For example, visual cue facility 308 may be configured to facilitate the display of a first visual cue by a first sound processor (e.g., corresponding to one or more fitting operations performed by way of the first sound processor) and facilitate the display of a second visual cue by a second sound processor (e.g., corresponding to one or more fitting operations performed by way of the second sound processor). In some examples, the first and second visual cues may be visually distinct one from another. For example, the first and second visual cues may have distinct blinking rates, colors, and/or any other visually distinguishable characteristic.

Visual cue facility 308 may be further configured to facilitate display of visual cues in a GUI. For example, visual cue facility 308 may be configured to provide data representative of visual cues to user interface facility 304 for display within a GUI. In some examples, the visual cues displayed within the GUI may coincide with visual cues displayed by one or more hardware components (e.g., one or more sound processors and/or CPI devices) communicatively coupled to fitting subsystem 202 along one or more communication paths. For example, the visual cues of the GUI may be displayed at the same time, may blink at the same rate, and/or may have the same color as the visual cues displayed by the hardware components.

Storage facility 310 may be configured to maintain fitting data 312 associated with one or more fitting operations, visual cue data 314 representative of one or more visual cues facilitated by visual cue facility 308, patient data 316 representative of data descriptive of or otherwise associated with one or more cochlear implant patients, control parameter data 318 representative of one or more control parameters, and program data 320 representative of one or more sound processing programs, any or all of which may be maintained within one or more data sets. Storage facility 310 may be configured to maintain additional or alternative data as may serve a particular implementation.

Figure 4:
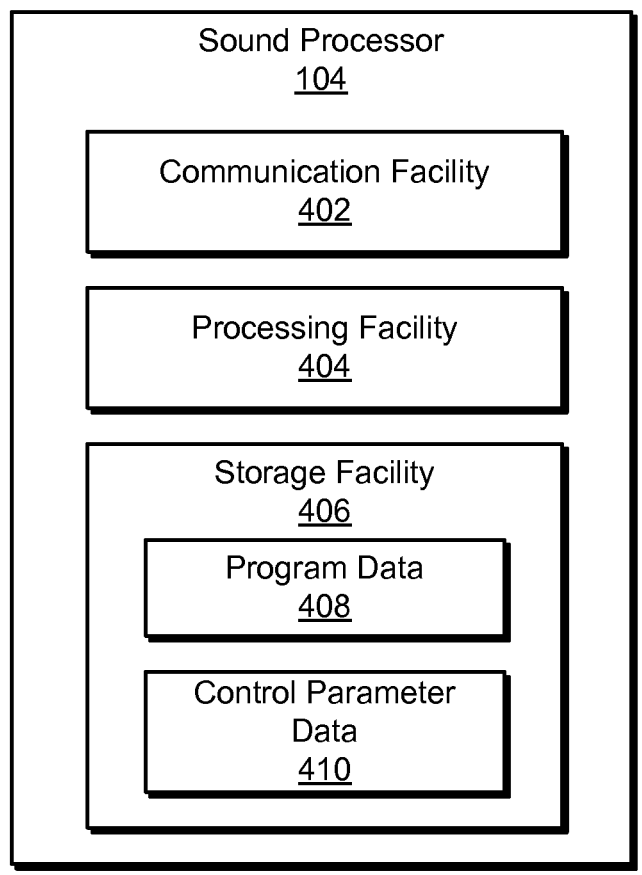
FIG. 4 illustrates exemplary components of a sound processor according to principles described herein.

FIG. 4 illustrates exemplary components of sound processor 104. As shown in FIG. 4, sound processor 104 may include a communication facility 402, a processing facility 404, and a storage facility 406, any or all of which may be in communication with one another using any suitable communication technologies. Each of these facilities will now be described in more detail.

Communication facility 402 may be configured to facilitate communication between sound processor 104 and fitting subsystem 202. For example, communication facility 402 may be configured to facilitate electrical coupling of sound processor 104 to a CPI device in order to communicate with fitting subsystem 202. Communication facility 402 may be further configured to facilitate communication between sound processor 104 and cochlear implant 110. For example, communication facility 402 may include transceiver components configured to wirelessly transmit data (e.g., control parameters and/or power signals) to cochlear implant 110 and/or wirelessly receive data from cochlear implant 110.

Processing facility 404 may be configured to perform one or more signal processing heuristics on an audio signal presented to the patient. For example, processing facility 404 may perform one or more pre-processing operations, spectral analysis operations, noise reduction operations, mapping operations, and/or any other types of signal processing operations on a detected audio signal as may serve a particular implementation. In some examples, processing facility 404 may generate and/or adjust one or more control parameters governing an operation of cochlear implant 110 (e.g., one or more stimulation parameters defining the stimulation pulses to be generated and applied by cochlear implant 110). In some examples, processing facility 404 may be configured to operate in accordance with one or more sound processing programs provided by fitting subsystem 202 and/or otherwise stored within storage facility 406.

Storage facility 406 may be configured to maintain program data 408 representative of one or more sound processing programs and control parameter data 410 representative of one or more control parameters. Storage facility 406 may be configured to maintain additional or alternative data as may serve a particular implementation.

Figure 5:
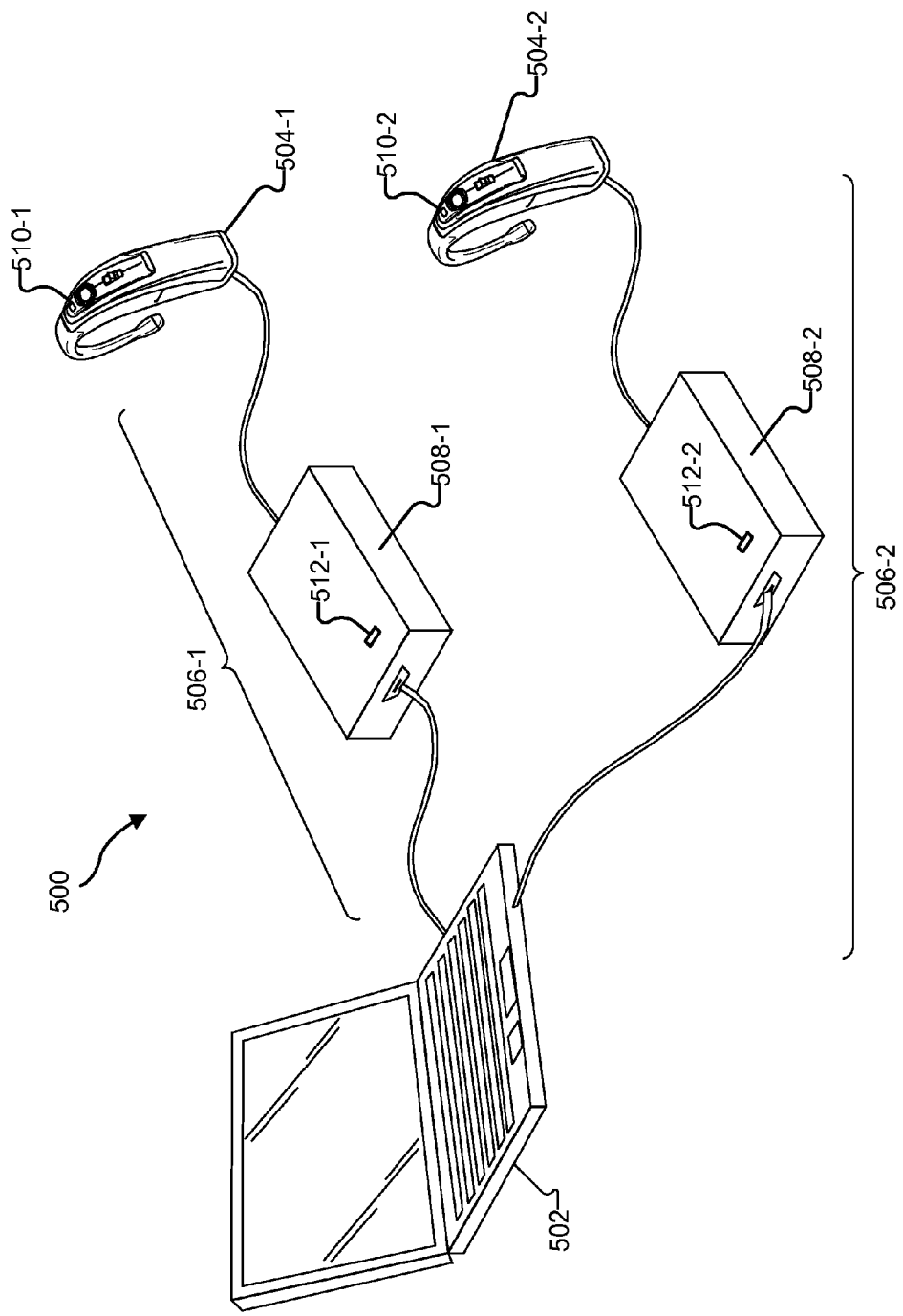
FIG. 5 illustrates an exemplary implementation of the cochlear implant fitting system of FIG. 2 according to principles described herein.

FIG. 5 illustrates an exemplary implementation 500 of fitting system 200 that may be used to fit a bilateral cochlear implant patient. In implementation 500, a fitting station 502 may be selectively and communicatively coupled to first and second BTE units 504-1 and 504-2 (collectively referred to herein as "BTE units 504") by way of corresponding communication paths 506-1 and 506-2 (collectively referred to herein as "communication paths 506") including one or more cables and CPI devices 508-1 and 508-2 (collectively referred to herein as "CPI devices 508"). BTE unit 504-1 may be associated with a first cochlear implant (e.g., a cochlear implant associated with a right ear of a patient), and BTE unit 504-2 may be associated with a second cochlear implant (e.g., a cochlear implant associated with a left ear of the patient). BTE units 504 are merely exemplary of the many different types of sound processors that may be used in accordance with the systems and methods described herein. Fitting station 502 may be selectively and communicatively coupled to any other type of sound processor and/or fitting hardware components as may serve a particular implementation.

Fitting station 502 may include any suitable computing device and/or combination of computing devices and may be configured to perform one or more of the fitting operations described herein. For example, fitting station 502 may display one or more GUIs configured to facilitate selection of one or more measurements to perform using BTE units 504, selection of one or more sound processing programs by which BTE units 504 operate, adjustment of one or more control parameters by which BTE units 504 operate, and/or any other fitting operation as may serve a particular implementation.

Communication paths 506 may be configured to facilitate communication between fitting station 502 and BTE units 504. In some examples, communication paths 506 may include one or more cables and/or intermediary hardware devices. For example, communication paths 506 may include CPI devices 508 selectively and communicatively coupled to fitting station 502 and/or BTE units 504 by way of one or more ports included within fitting station 502 and BTE units 504.

BTE units 504 may include LEDs 510-1 and 510-2 (collectively referred to herein as "LEDs 510"). LEDs 510 may be configured to selectively illuminate in accordance with one or more normal operations of LEDs 510 and/or BTE units 504. For example, LEDs 510 may be configured to illuminate to provide information associated with BTE units 504 (e.g., to indicate battery levels of BTE units 504, to indicate that BTE units 504 are connected or "locked" to corresponding cochlear implants, to indicate that BTE units 504 are powered on, etc.). In some examples, the one or more normal operations of LEDs 510 may be overridden to display one or more visual cues. For example, fitting station 502 may be configured to transmit one or more signals by way of communication paths 506 to BTE units 504, the one or more signals configured to override a normal operation of LEDs 510 and/or BTE units 504 to selectively illuminate LEDs 510 to display the one or more visual cues.

CPI devices 508 may include LEDs 512-1 and 512-2 (collectively referred to herein as "LEDs 512"). LEDs 512 may be configured to selectively illuminate in accordance with one or more normal operations of LEDs 512 and/or CPI devices 508. For example, LEDs 512 may be configured to illuminate to provide information associated with CPI devices 508 (e.g., to indicate that CPI devices 508 are powered on). In some examples, the one or more normal operations of LEDs 512 and/or CPI devices 508 may be overridden to display one or more visual cues. For example, fitting station 502 may be configured to transmit one or more signals by way of communication paths 506 to CPI devices 508, the one or more signals configured to override a normal operation of LEDs 512 and/or CPI devices 508 to selectively illuminate LEDs 512 to display the one or more visual cues.

In an alternative implementation, CPI devices 508 may be replaced by a single CPI device configured to interface between fitting station 502 and both BTE units 504 (e.g., both BTE units 504 may connect to the single CPI device, which in turn may connect to fitting station 502). In some examples, the single CPI device may include two LEDs (e.g., the single CPI device may include a first LED associated with first BTE unit 504-1 and a second LED associated with second BTE unit 504-2). The two LEDs of the single CPI device may be configured to display one or more visual cues in accordance with one or more methods or operations disclosed herein. For example, a first LED may of the single CPI device may be configured to display at least one visual cue in conjunction with a fitting operation performed by first BTE unit 504-1 and a second LED of the single CPI device may be configured to display at least one other visual cue in conjunction with a fitting operation performed by second BTE unit 504-2. In a yet further implementation, fitting station 502 may be connected to, and may be configured to provide one or more visual cues by way of, any number of CPI devices and/or corresponding BTE units.

Figure 6:
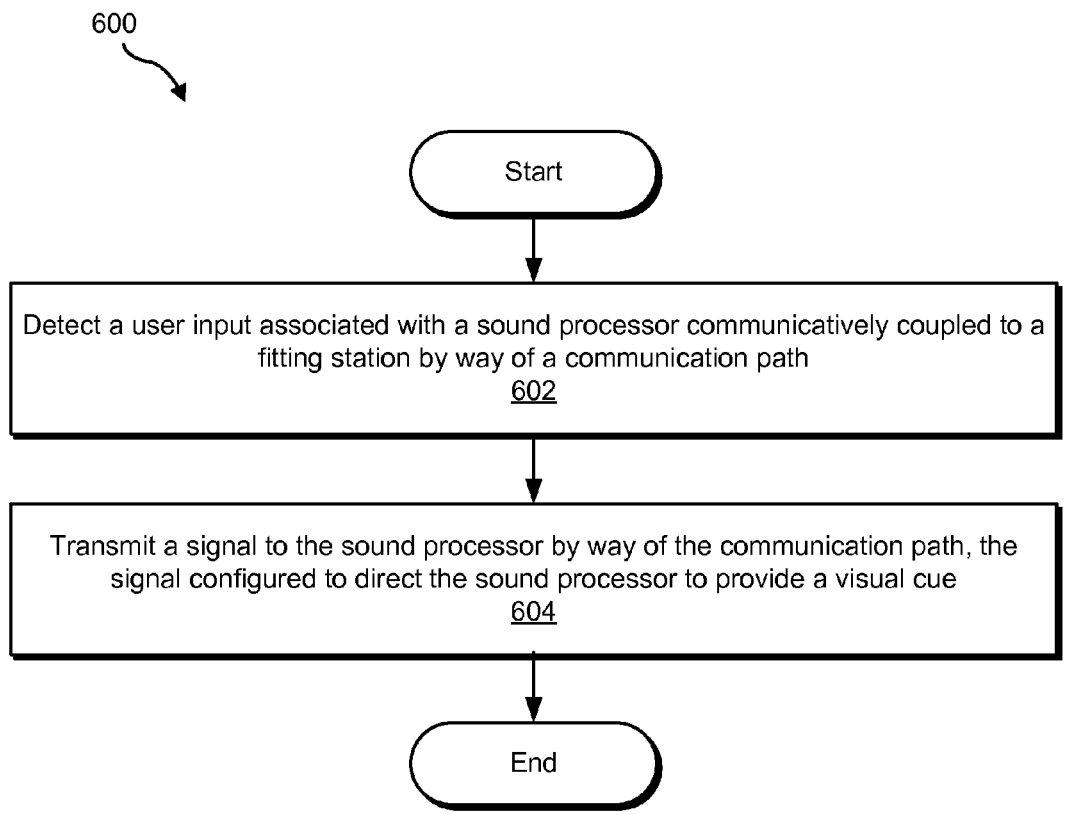
FIG. 6 illustrates an exemplary method of presenting visual cues to assist in fitting a cochlear implant patient according to principles described herein.

FIG. 6 illustrates an exemplary method 600 of providing visual cues to assist in fitting a cochlear implant patient. While FIG. 6 illustrates exemplary steps according to one embodiment, other embodiments may omit, add to, reorder, and/or modify any of the steps shown in FIG. 6. One or more of the steps shown in FIG. 6 may be performed by any component or combination of components of fitting subsystem 202 and/or fitting station 502.

In step 602, a fitting station detects a user input associated with a sound processor communicatively coupled to the fitting station by way of a communication path. For example, user interface facility 304 may be configured to detect a user input associated with a sound processor communicatively coupled to fitting subsystem 202 by way of a communication path.

Figure 7:
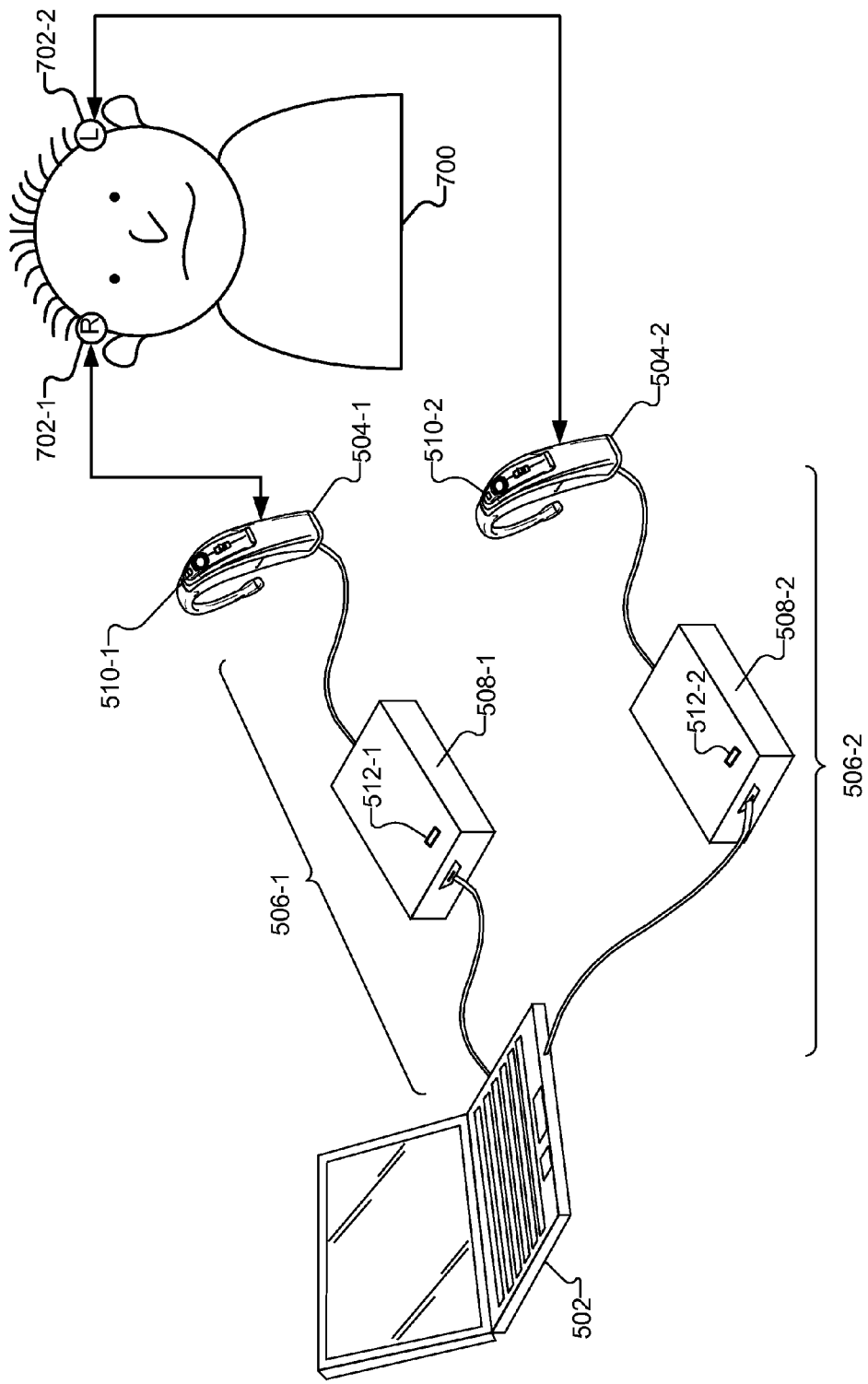
FIG. 7 shows an exemplary bilateral cochlear implant patient being fitted by the fitting components described in connection with FIG. 5 according to principles described herein.

To illustrate, FIG. 7 shows an exemplary bilateral cochlear implant patient 700 (or simply "patient 700") being fitted by the fitting components described in connection with FIG. 5. As shown in FIG. 7, patient 700 may have a first cochlear implant 702-1 associated with a first ear (e.g., the right ear) and a second cochlear implant 702-2 associated with a second ear (e.g., the left ear). Cochlear implants 702-1 and 702-2 (collectively referred to herein as "cochlear implants 702") may be implanted in patient 700 using any suitable technique as may serve a particular implementation.

An audiologist may use fitting station 502 to communicate with first BTE unit 504-1 by way of first communication path 506-1 to fit first cochlear implant 702-1 and/or first BTE unit 504-1 to patient 700. The audiologist may likewise use fitting station 502 to communicate with second BTE unit 504-2 by way of second communication path 506-2 to fit second cochlear implant 702-2 and/or second BTE unit 504-2 to patient 700. For example, fitting station 502 may direct first cochlear implant 702-1 by way of first communication path 506-1 and BTE unit 504-1 to perform one or more fitting operations to fit first cochlear implant 702-1 to patient 700 and direct second cochlear implant 702-2 by way of second communication path 506-2 and BTE unit 504-2 to perform one or more fitting operations to fit second cochlear implant 702-2 to patient 700.

During the fitting process, fitting station 502 may be configured to detect user input (e.g., user input provided by an audiologist) associated with BTE units 504. For example, fitting station 502 may be configured to detect one or more user input commands to perform one or more fitting operations by way of first BTE unit 504-1 and/or one or more user input commands requesting that one or more visual cues be displayed by first BTE unit 504-1. Fitting station 502 may be further configured to detect any other suitable user input associated with BTE units 504 and/or cochlear implants 702.

Returning to FIG. 6, in step 604, a fitting station transmits a signal to the sound processor by way of the communication path, the signal configured to direct the sound processor to display a visual cue. The fitting station may be configured to transmit the signal and the sound processor may be configured to display the visual cue in any suitable manner.

Figure 8:
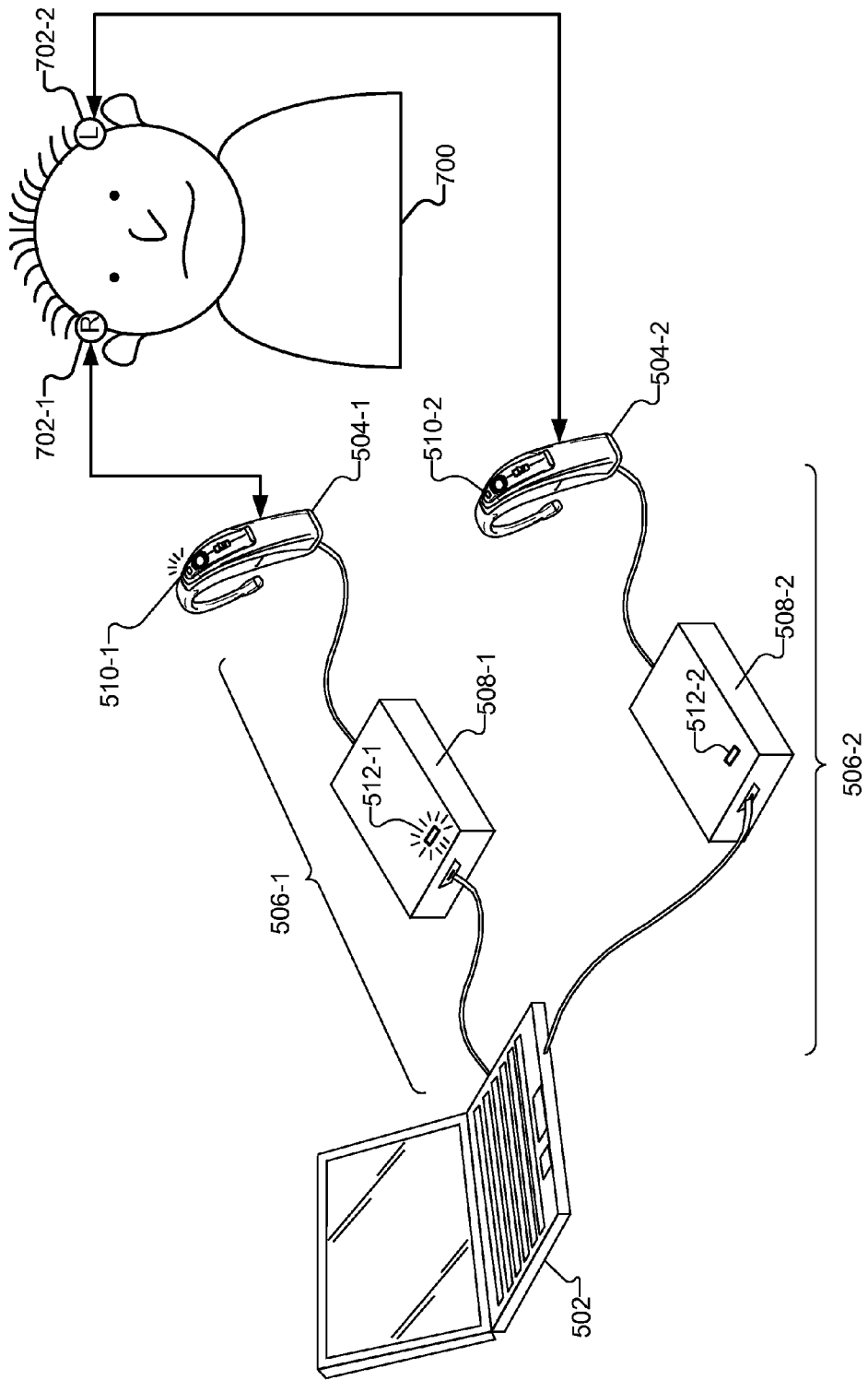
FIG. 8 shows the fitting components of FIG. 7 being used to provide a visual cue according to principles described herein.

To illustrate, FIG. 8 shows fitting components of FIG. 7 displaying a visual cue in response to a detection of a user input associated with first BTE unit 504-1. In response to the detection of the user input, for example, fitting station 502 may transmit a signal to first BTE unit 504-1 by way of first communication path 506-1. The signal may be configured to direct first BTE unit 504-1 to display a visual cue. For example, the signal may be configured to override a normal operation of LED 510-1 to selectively illuminate LED 510-1, as depicted in FIG. 8. The signal may be further configured to direct first CPI device 508-1 to display an additional visual cue. For example, the signal may be configured to override a normal operation of LED 512-1 to selectively illuminate LED 512-1, as depicted in FIG. 8. In some examples, the illumination of LED 512-1 may be coordinated with the illumination of LED 510-1 (e.g., LED 510-1 and LED 512-1 may illuminate at the same time, may illuminate in the same color, and/or may blink at the same rate).

As a result, an audiologist using fitting station 502 may visually verify that fitting station 502 is properly connected to first BTE unit 504-1 and/or that a fitting operation will be or is being performed by first BTE unit 504-1 in response to the user input.

In some examples, fitting station 502 may be configured to prompt a user for a confirmation of a user input command. The prompt may be provided in conjunction with the visual cue and prior to executing the user input command. To illustrate, in response to a user input command to initialize (e.g., reformat) first BTE unit 504-1, fitting station may transmit a signal to direct first BTE unit 504 to display the visual cue, as shown in FIG. 8. As the visual cue is being provided, fitting station 502 may prompt the user for confirmation of the user input command to initialize first BTE unit 504-1 prior to executing the initialization of first BTE unit 504-1. As a result, the user can visually verify that the intended BTE unit (e.g., first BTE unit 504-1) will be initialized, thereby avoiding an inadvertent reformatting of the wrong BTE unit (e.g., second BTE unit 504-2). In response to receiving a confirmation of the user input command from the user, fitting station 502 may proceed with the initialization of first BTE unit 504-1.

FIG. 8 is provided for illustrative purposes only. Fitting station 502 may be configured to direct first CPI device 508-1 and/or BTE unit 504-1 to display one or more visual cues in any other suitable manner.

Figure 9:
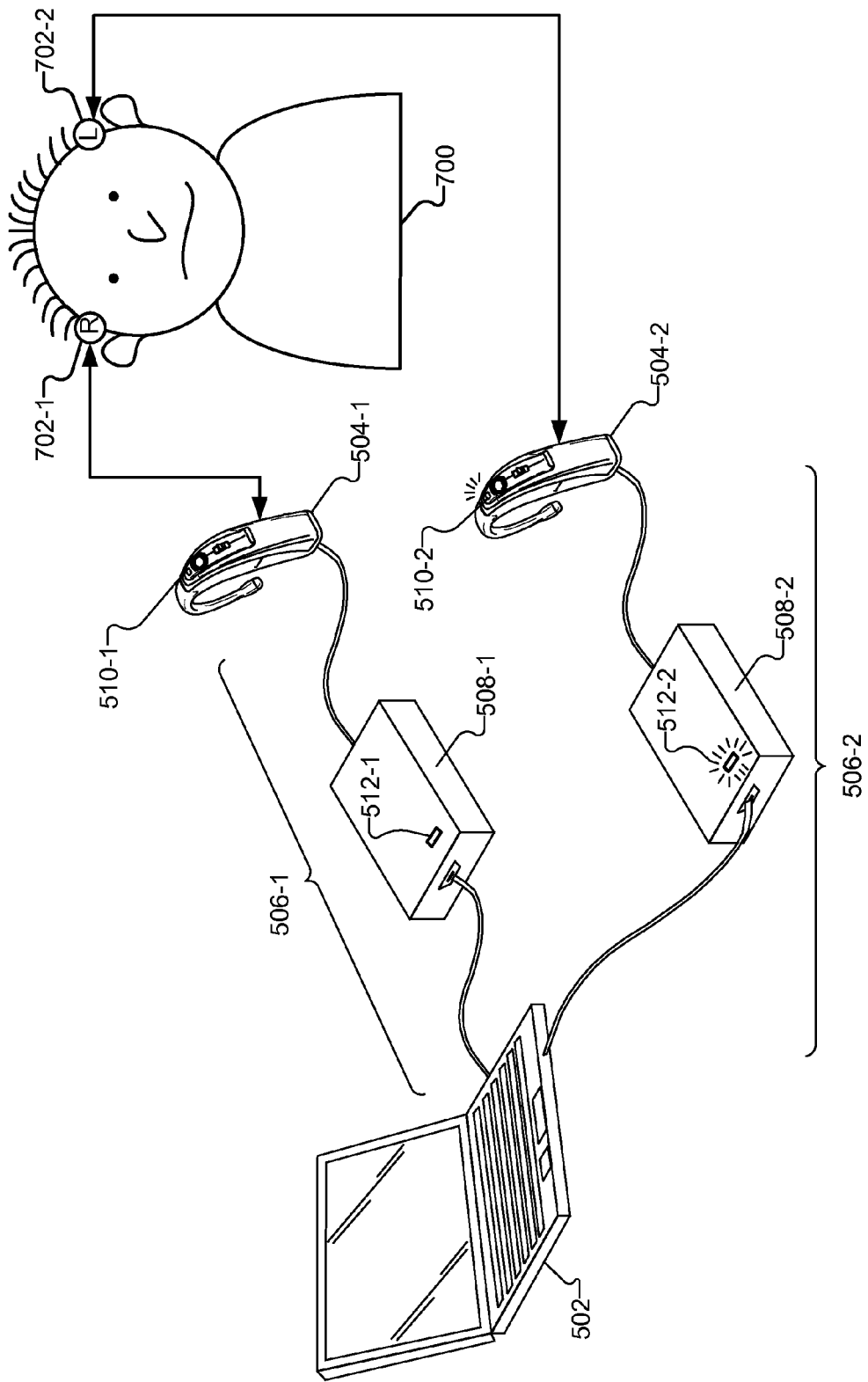
FIG. 9 shows the fitting components of FIG. 7 being used to provide an additional visual cue according to principles described herein.

In additional or alternative examples, fitting station 502 may be configured to transmit a second signal to second BTE unit 504-2 by way of second communication path 506-2, the second signal configured to direct second BTE unit 504-2 to display a second visual cue. For example, as shown in FIG. 9, in response to a detection of a user input associated with second BTE unit 504-2, fitting station 502 may transmit a second signal by way of second communication path 506-2. The second signal may be configured to direct LED 510-2 to selectively illuminate (e.g., by overriding the normal operations of LED 510-2 and/or BTE unit 504-2) to display the second visual cue as illustrated in FIG. 9. The second signal may also be configured to direct LED 512-2 to selectively illuminate (e.g., by overriding the normal operations of LED 512-2) to display an additional second visual cue as illustrated in FIG. 9. In some examples, the visual cues displayed by BTE unit 504-2 and/or CPI device 508-2 may be visually distinguishable from the visual cues displayed by first BTE unit 504-1 and first CPI device 508-1.

Figure 10:
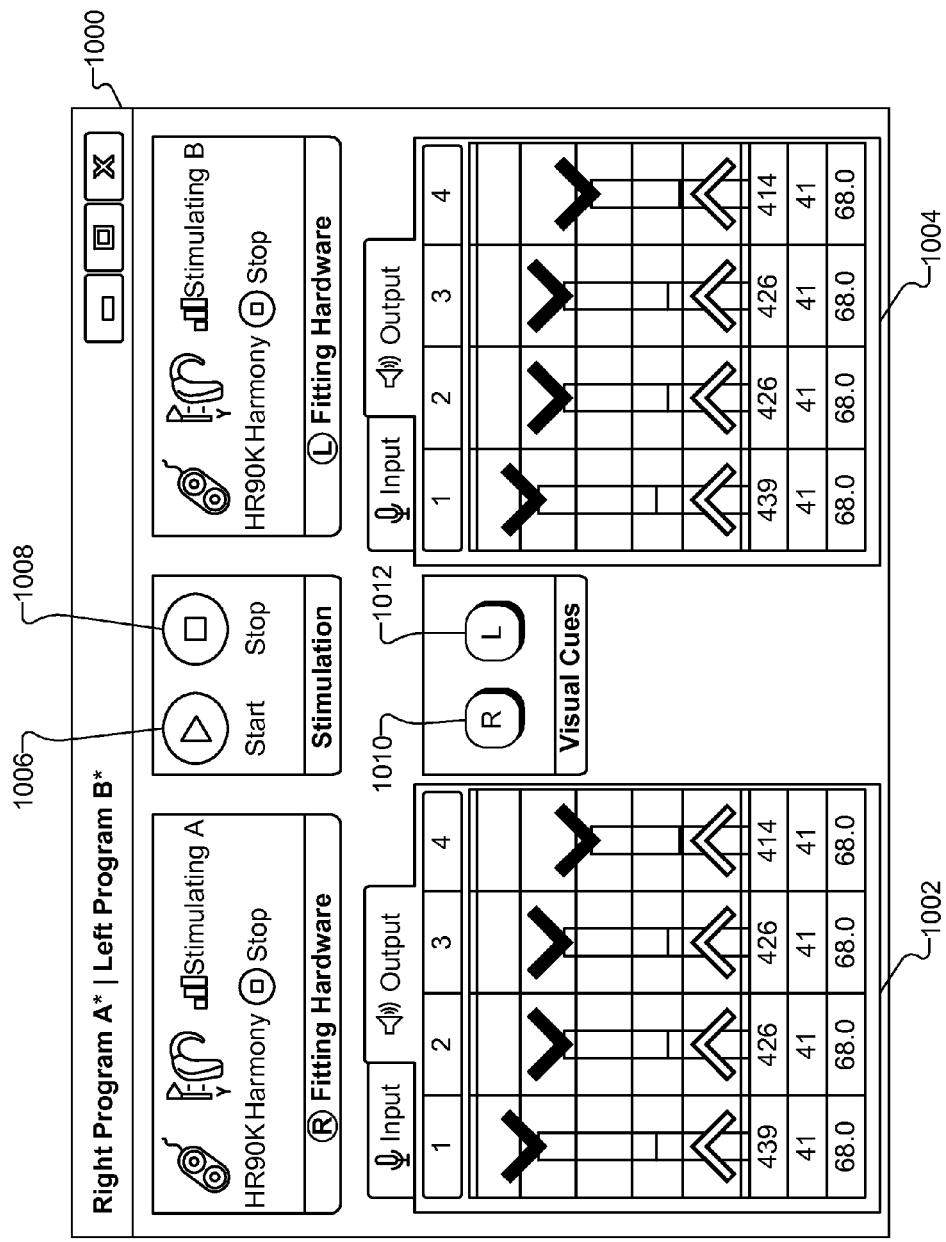
FIG. 10 illustrates an exemplary graphical user interface ("GUI") that may be used to fit a cochlear implant patient according to principles described herein.

In some examples, the user input commands may be received by way of a graphical user interface ("GUI"). For example, FIG. 10 illustrates an exemplary GUI 1000 that may be provided for display by fitting subsystem 202 and that may be used to fit a bilateral cochlear implant patient. As shown in FIG. 10, GUI 1000 may graphically indicate one or more fitting operations being performed to fit a cochlear implant to the patient. For example, viewing portion 1002 may graphically indicate a presentation of stimulation pulses performed by a cochlear implant associated with the right ear of the patient, and viewing portion 1004 may graphically indicate a presentation of stimulation pulses performed by a cochlear implant associated with the left ear of the patient. GUI 1000 may display options 1006 and 1008 that may be selected by a user to "Start" or "Stop" a fitting operation. GUI 1000 may also display an option 1010 that may be selected by a user to request that a visual cue be displayed by a sound processor associated with viewing portion 1002 and/or the patient's right ear. GUI 1000 may also display an option 1012 that may be selected by a user to request that a visual cue be displayed by a sound processor associated with viewing portion 1004 and/or the patient's left ear. Any other option associated with fitting a cochlear implant patient may be displayed within GUI 1000 as may serve a particular implementation.

In some examples, GUI 1000 may be configured to display one or more visual cues in conjunction with visual cues displayed by one or more associated hardware components. For example, viewing portion 1002 may be displayed in a first color corresponding to the patient's right ear and/or hardware components associated with the patient's right ear, and viewing portion 1004 may be displayed in a second color corresponding to the patient's left ear and/or hardware components associated with the patient's left ear. Additionally or alternatively, viewing portion 1002 may be configured to display any other suitable visual cue (e.g., may be configured to flash, blink, etc.) that corresponds with a visual cue displayed by hardware components associated with viewing portion 1002, and viewing portion 1004 may be configured to display any other suitable visual cue that corresponds with a visual cue displayed by hardware components associated with viewing portion 1004. In some examples, options 1010 and/or 1012 may be configured to provide visual cues in conjunction with one or more visual cues presented by one or more hardware components associated with options 1010 and 1012. For example, options 1010 and/or 1012 may be displayed using one or more colors and/or patterns that coincide with one or more colors and/or patterns associated with visual cues presented by one or more hardware components associated with options 1010 and 1012. For instance, option 1010 may blink synchronously with the blinking of an LED of a hardware component associated with option 1010. Such visual cues within GUI 1000 may help an audiologist to visually discern which chain of hardware fitting components is associated with which GUI feature (e.g., viewing portion 1002 or 1004, option 1010 or 1012, etc.). For example, a visual cue displayed in GUI 1000 may indicate whether first BTE unit 504-1 is associated with viewing portion 1002 or 1004.

Figure 11:
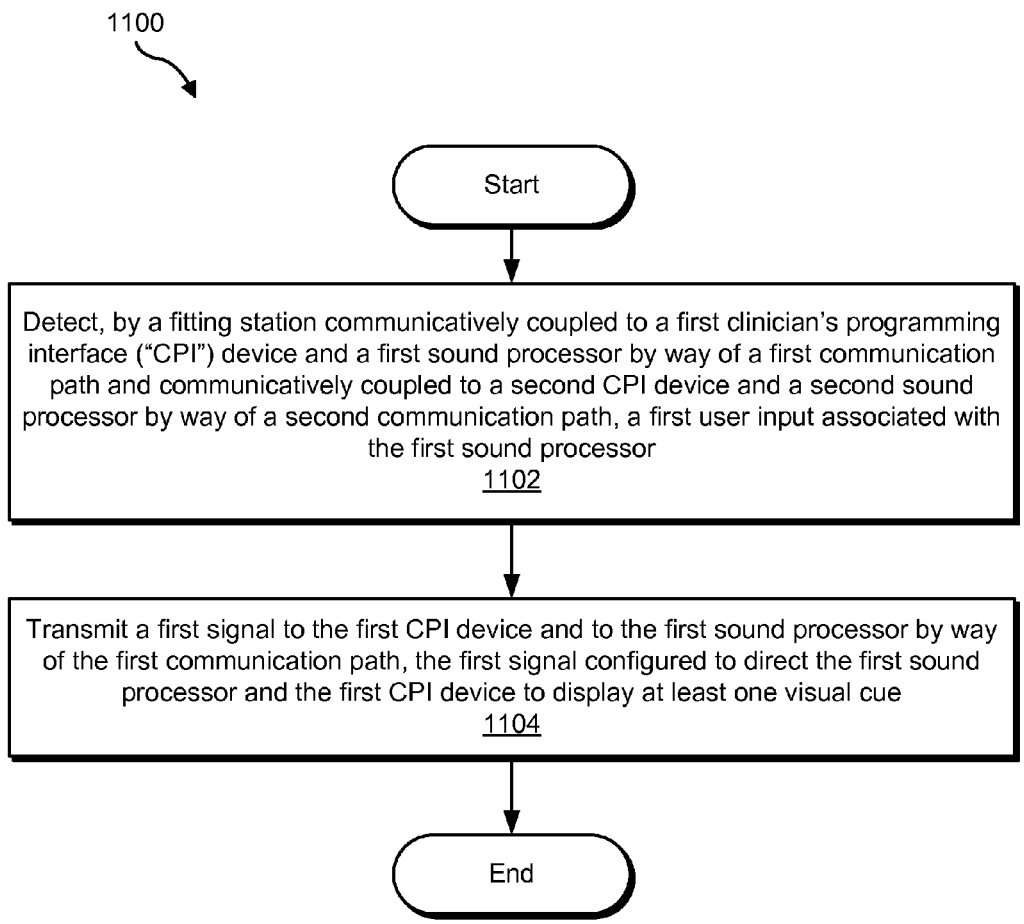
FIG. 11 illustrates another exemplary method of providing visual cues to assist in fitting a bilateral cochlear implant patient according to principles described herein.

FIG. 11 illustrates another exemplary method 1100 of providing visual cues to assist in fitting a cochlear implant patient. While FIG. 11 illustrates exemplary steps according to one embodiment, other embodiments may omit, add to, reorder, and/or modify any of the steps shown in FIG. 11. One or more of the steps shown in FIG. 11 may be performed by any component or combination of components of fitting subsystem 202 and/or fitting station 502.

In step 1102, a fitting station detects a first user input associated with a first sound processor. The fitting station is communicatively coupled to the first sound processor and a first CPI device by way of a first communication path. The fitting station is also communicatively coupled to a second sound processor and a second CPI device by way of a second communication path. The fitting station may be configured to detect the user input associated with the first sound processor in any suitable manner, such as described herein.

In step 1104, the fitting station transmits a first signal to the first CPI device and to the first sound processor by way of the first communication path. The first signal is configured to direct the first sound processor and the first CPI device to display at least one visual cue. The fitting station may be configured to transmit the signal in any suitable manner, and the first CPI Device and the first sound processor may be configured to display the at least one visual cue in any suitable manner, such as described herein.

In certain embodiments, one or more of the processes described herein may be implemented at least in part as instructions executable by one or more computing devices. In general, a processor (e.g., a microprocessor) receives instructions, from a tangible computer-readable medium, (e.g., a memory, etc.), and executes those instructions, thereby performing one or more processes, including one or more of the processes described herein. Such instructions may be stored and/or transmitted using any of a variety of known non-transitory computer-readable media.

A non-transitory computer-readable medium (also referred to as a processor-readable medium) includes any non-transitory medium that participates in providing data (e.g., instructions) that may be read by a computer (e.g., by a processor of a computer). Such a non-transitory medium may take many forms, including, but not limited to, non-volatile media and/or volatile media. Non-volatile media may include, for example, optical or magnetic disks and other persistent memory. Volatile media may include, for example, dynamic random access memory ("DRAM"), which typically constitutes a main memory. Common forms of non-transitory computer-readable media include, for example, a floppy disk, flexible disk, hard disk, magnetic tape, any other magnetic medium, a CD-ROM, DVD, any other optical medium, a RAM, a PROM, an EPROM, a FLASH-EEPROM, any other memory chip or cartridge, or any other non-transitory medium from which a computer can read.

Figure 12:
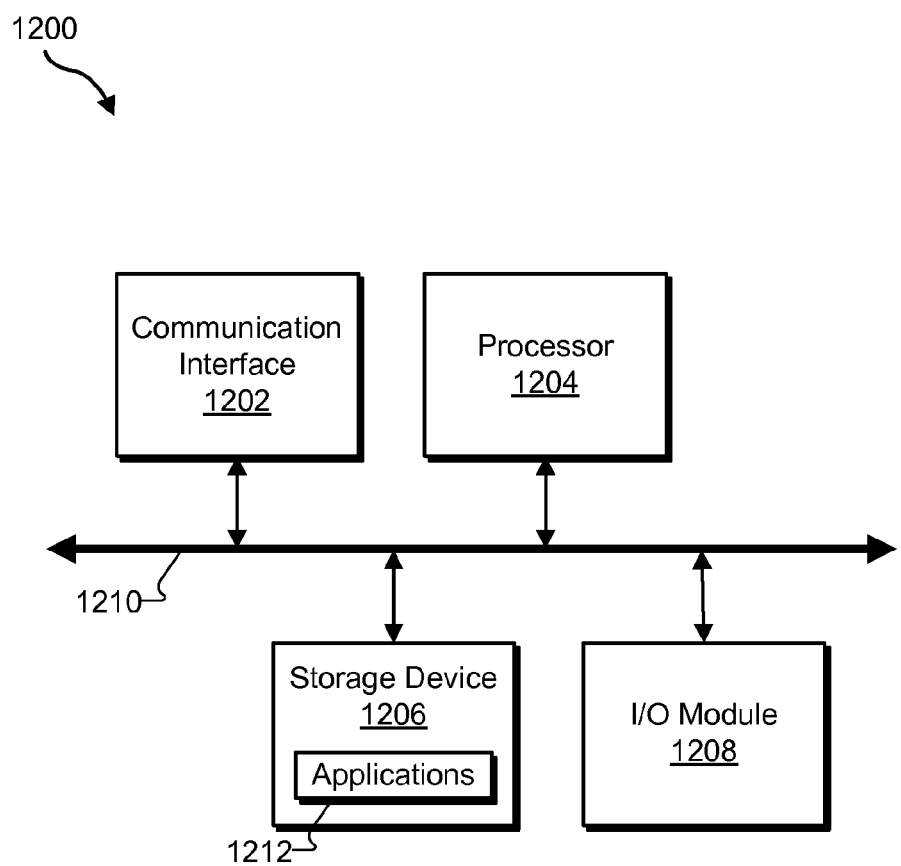
FIG. 12 illustrates an exemplary computing device according to principles described herein.

FIG. 12 illustrates an exemplary computing device 1200 that may be configured to perform one or more of the processes described herein. As shown in FIG. 12, computing device 1200 may include a communication interface 1202, a processor 1204, a storage device 1206, and an input/output ("I/O") module 1208 communicatively connected via a communication infrastructure 1210. While an exemplary computing device 1200 is shown in FIG. 12, the components illustrated in FIG. 12 are not intended to be limiting. Additional or alternative components may be used in other embodiments. Components of computing device 1200 shown in FIG. 12 will now be described in additional detail.

Communication interface 1202 may be configured to communicate with one or more computing devices. Examples of communication interface 1202 include, without limitation, a wired network interface (such as a network interface card), a wireless network interface (such as a wireless network interface card), a modem, and any other suitable interface. Communication interface 1202 may additionally or alternatively provide such a connection through, for example, a local area network (such as an Ethernet network), a personal area network, a telephone or cable network, a satellite data connection, a dedicated URL, or any other suitable connection. Communication interface 1202 may be configured to interface with any suitable communication media, protocols, and formats, including any of those mentioned above.

Processor 1204 generally represents any type or form of processing unit capable of processing data or interpreting, executing, and/or directing execution of one or more of the instructions, processes, and/or operations described herein. Processor 1204 may direct execution of operations in accordance with one or more applications 1212 or other computer-executable instructions such as may be stored in storage device 1206 or another non-transitory computer-readable medium.

Storage device 1206 may include one or more data storage media, devices, or configurations and may employ any type, form, and combination of data storage media and/or device. For example, storage device 1206 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 1206. For example, data representative of one or more executable applications 1212 (which may include, but are not limited to, one or more of the software applications described herein) configured to direct processor 1204 to perform any of the operations described herein may be stored within storage device 1206. In some examples, data may be arranged in one or more databases residing within storage device 1206.

I/O module 1208 may be configured to receive user input and provide user output and may include any hardware, firmware, software, or combination thereof supportive of input and output capabilities. For example, I/O module 1208 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1208 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 1208 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1200. For example, one or more applications 1212 residing within storage device 1206 may be configured to direct processor 1204 to perform one or more processes or functions associated with communication facility 302, user interface facility 304, fitting facility 306, visual cue facility 308, communication facility 402, and/or processing facility 404. Likewise, storage facility 310 and/or storage facility 406 may be implemented by or within storage device 1206.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, in certain embodiments, the one or more visual cues described herein may be replaced by, or provided simultaneously with, one or more auditory cues and/or one or more vibration cues. Accordingly, for example, a fitting station may be configured to direct a sound processor and/or CPI device to produce an audible sound and/or to vibrate in conjunction with a fitting operation, thereby allowing a user (e.g., an audiologist) to verify what hardware is performing the fitting operation. In addition, certain features of one embodiment described herein may be combined with or substituted for features of another embodiment described herein. The description and drawings are accordingly to be regarded in an illustrative rather than a restrictive sense.

What is claimed is:

1. A method comprising:
   detecting, by a cochlear implant fitting station, a user input command for a sound processor included in a cochlear implant system to perform one or more cochlear implant fitting operations, wherein the sound processor is communicatively coupled to the cochlear implant fitting station by way of a communication path;
   directing, by the cochlear implant fitting station in response to the user input command, the sound processor to perform the one or more cochlear implant fitting operations; and
   transmitting, by the cochlear implant fitting station in response to the user input command, a signal to the sound processor by way of the communication path, the signal configured to direct the sound processor to display a visual cue prior to or simultaneously with the performance of the one or more cochlear implant fitting operations.

2. The method of claim 1, wherein:
   the sound processor comprises a light emitting diode ("LED"); and
   the signal is configured to override a normal operation of the LED to display the visual cue.

3. The method of claim 2, wherein the signal is configured to cause the LED to blink intermittently.

4. The method of claim 3, wherein the communication path includes one or more intermediary hardware devices communicatively coupled to the cochlear implant fitting station and the sound processor.

5. The method of claim 4, wherein:
   the one or more intermediary hardware devices include a clinician's programming interface ("CPI") device; and
   the transmitting the signal to the sound processor by way of the communication path comprises transmitting the signal to the sound processor by way of the CPI device, wherein the signal is further configured to direct the CPI device to display an additional visual cue.

6. The method of claim 5, wherein:
   the CPI device comprises an LED; and
   the signal is further configured to override a normal operation of the LED of the CPI device to display the additional visual cue.

7. The method of claim 6, wherein the signal is further configured to cause the LED of the CPI device to blink intermittently in synchronization with the LED of the sound processor.

8. A method comprising:
   detecting, by a cochlear implant fitting station, a user input command to initialize a sound processor included in a cochlear implant system, wherein the sound processor is communicatively coupled to the cochlear implant fitting station by way of a communication path; and
   transmitting, by the cochlear implant fitting station in response to the detecting, a signal to the sound processor by way of the communication path, the signal configured to direct the sound processor to display a visual cue;
   prompting, by the cochlear implant fitting station in conjunction with the visual cue, a user for a confirmation of the user input command;
   receiving, by the cochlear implant fitting station, the confirmation of the user input command from the user; and
   initializing, by the cochlear implant fitting station in response to the receiving the confirmation, the sound processor.

9. The method of claim 1, wherein the user input command further comprises a command to display the visual cue.

10. The method of claim 1, further comprising providing, by the cochlear implant fitting station, a graphical user interface configured to facilitate interaction by a user with the sound processor.

11. The method of claim 10, wherein the graphical user interface is further configured to display an additional visual cue in conjunction with the providing of the visual cue by the sound processor.

12. The method of claim 1, embodied as computer-executable instructions on at least one non-transitory computer-readable medium.

13. The method of claim 8, wherein:
the sound processor comprises a light emitting diode ("LED"); and
the signal is configured to override a normal operation of the LED to display the visual cue.

14. The method of claim 13, wherein the signal is configured to cause the LED to blink intermittently.

15. The method of claim 14, wherein the communication path includes one or more intermediary hardware devices communicatively coupled to the cochlear implant fitting station and the sound processor.

16. The method of claim 15, wherein:
the one or more intermediary hardware devices include a clinician's programming interface ("CPI") device; and
the transmitting the signal to the sound processor by way of the communication path comprises transmitting the signal to the sound processor by way of the CPI device, wherein the signal is further configured to direct the CPI device to display an additional visual cue.

17. The method of claim 16, wherein:
the CPI device comprises an LED; and
the signal is further configured to override a normal operation of the LED of the CPI device to display the additional visual cue.

18. The method of claim 17, wherein the signal is further configured to cause the LED of the CPI device to blink intermittently in synchronization with the LED of the sound processor.

* * * * *